United States Patent [19]

Huang et al.

[11] 4,269,846
[45] May 26, 1981

[54] HETEROCYCLIC COMPOUNDS USEFUL AS ANTI-ALLERGY AGENTS

[75] Inventors: Fu C. Huang, Boonton, N.J.; John H. Musser, Hawthorne, N.Y.

[73] Assignee: USV Pharmaceutical Corporation, Tuckahoe, N.Y.

[21] Appl. No.: 89,246

[22] Filed: Oct. 29, 1979

[51] Int. Cl.[3] .................. A61K 31/41; C07D 271/10; C07D 285/12; C07D 249/02
[52] U.S. Cl. .................................... 424/269; 424/270; 424/272; 424/273 R; 548/136; 548/137; 548/144; 548/152; 548/219; 548/263
[58] Field of Search ............... 548/144, 142, 263, 152, 548/219, 137, 136; 424/269, 270, 272, 273 R

[56] References Cited

PUBLICATIONS

Sawhney et al., "Chem. Abs.", vol. 82, (1975) 156188w.
Pilgram et al., "J. Heteocyclic Chem.", vol. 13, (1976), 1257-1263.

Primary Examiner—Anton H. Sutto
Attorney, Agent, or Firm—Leon E. Tenenbaum

[57] ABSTRACT

New benzoheterocyclic oxadiazolones and triazolones are described. These compounds are useful as anti-allergic reagents.

21 Claims, No Drawings

HETEROCYCLIC COMPOUNDS USEFUL AS ANTI-ALLERGY AGENTS

This invention relates to new anti-allergy agents and more particularly to new heterocyclic compounds useful by virtue of their anti-allergy activity.

Oxadiazolones are known in the literature, having the following structure:

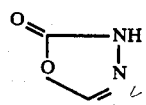

as are analogous heterocycles in which O is replaced by S, NH or $CH_2$ with or without substituents in place of H.

Pyridyl, quinolyl, furyl and thienyloxadiazolones were described in J.A.C.S. 76, 2208 (1954); pyridazyloxadiazolone in Khim. Geterosikl, Svedin, 556 (1973); nitroimidazolyloxadiazolone as anti-bacterial in German Specification 2,045,789 (1971); indolyloxadiazolone in Tet. Let. 3235 (1973); and methyl isoxazolyloxadiazolone as an antilepral agent in J. Org. Chem. 26, 1514 (1961).

The new heterocyclic compounds of the present invention are benzoheterocycles of the following formula:

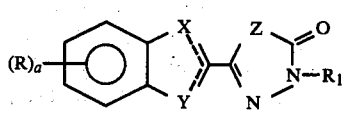

wherein, the dotted line indicates that the double bond may be in either position;

R is H, alkyl, alkenyl, alkynyl, aryl, aralkyl, aralkenyl, hydroxy, alkoxy, alkenyloxy, alkynyloxy, aryloxy, aralkyloxy, halogen, cyano, nitro, carboxy, formyl, carbalkoxy, carbaryloxy, hydroxyalkyl, amino, alkylamino, trifluoromethyl, mercapto, trifluoromethoxy, alkylthio or aminoalkyl;

Y is N, $NR_2$ or C—$R_2$ wherein $R_2$ is H, alkyl or aryl with the proviso that when Y is NH, $R_a$ is not H;

a is an integer from 1 to 4;

X and Z are each O, S, $NR_2$ or $CR_2$ wherein $R_2$ is as defined above with the proviso that when Y is $NR_2$, X is not $CR_2$; and $R_1$ is H, alkyl, aryl, acyl, carbalkoxy, or carbaryloxy.

The total number of carbon atoms in each such hydrocarbyl substituent representative of R, $R_1$, $R_z$, Z and X can range up to about 10 carbon atoms. The preferred compounds are those in which the said hydrocarbyl radicals contain up to about 7 carbon atoms when aliphatic and up to 10 carbon atoms when aromatic, e.g., phenyl and naphthyl. The aryl, aralkyl and alkaryl radicals also are intended to include the known heterocyclic rings such as furan, thiophene, thiazole, pyridine, pyrimidine, piperidine, oxazole, and the like, as well as benzo-heterocycles such as benzothiophene and benzofuran. Although up to four substituents are indicated in the definition of $(R)_2(a=1-4)$, it is preferred to have not more than 2 substituents on the benzenoid moiety. The preferred compounds are those in which both X and Z are oxygen and Y is nitrogen and those in which X is NH, N-alkyl, or N-aryl; Z is O; and Y is N.

The new compounds of this invention can be prepared by art-recognized procedures from known starting compounds. Exemplary procedures for preparation of benzoheterocyclic oxadiazolones involve ring closure of the following compounds:

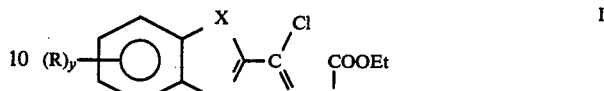

I

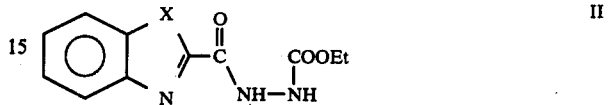

II

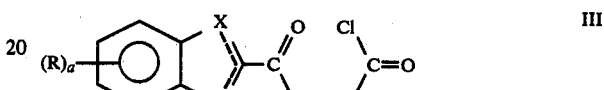

III

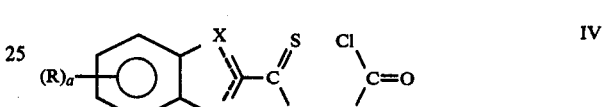

IV

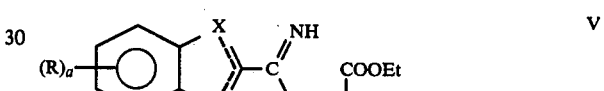

V

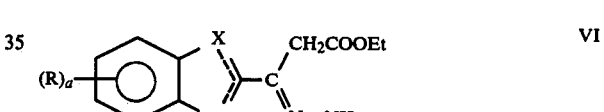

VI which can be prepared by known procedures, e.g.,

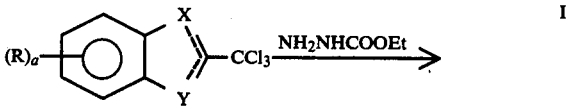

I

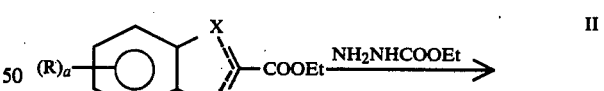

II

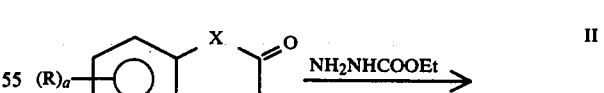

II

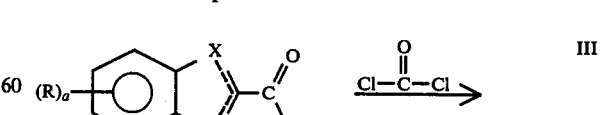

III

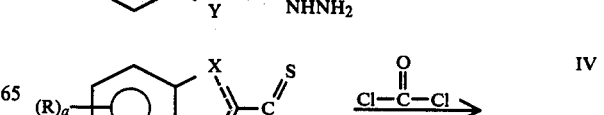

IV

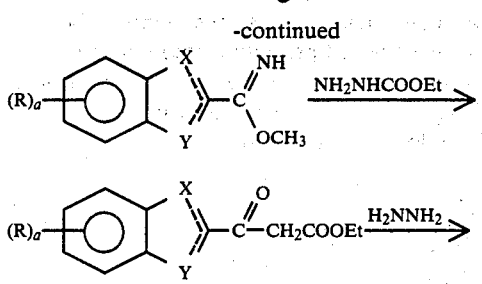

Employing similar procedures, analogous heterocyclics can be formed wherein Z is other than O.

Substituents on the oxadiazolone nucleus can be introduced either by employing appropriately substituted hydrazine in the ring formation reaction, or by alkylation or acylation reactions of the already formed ring.

Substituents on the aromatic ring which are reactive and which would interfere with the ring closure reactions are best introduced by subsequent reactions standard to the art, for example, reduction of a nitro to an amino group or hydrolysis of a cyano to an amide or an acid.

Using the procedures described, a wide variety of heterocyclics can be prepared, as follows:

| $(R)_y$ | Y | X | Z | $R_1$ |
|---|---|---|---|---|
| H | N | S | O | H |
| 5-$CH_3$ | N | $CH_2$ | O | $CH_3$ |
| 6-$CH_3$ | N | $CH(C_6H_5)$ | S | H |
| 5-Cl | N | $NCH_3$ | NH | H |
| 6-$OCH_3$ | N | NH | O | $C_6H_5CH_2$ |
| 6-$OCH_3$ | N | O | O | H |
| 5-$C_6H_5$ | N | S | O | H |
| 5-$CF_3$ | N | $NC_6H_5$ | O | $CH_3$ |
| 5-$OC_3H_5$ | N | $CH_2$ | O | $COOCH_3$ |
| 6-$OC_6H_5$ | N | NH | $CHCH_3$ | $CH_3CO$ |
| H | N | $CH_2$ | S | H |
| 6-OH | N | $NCH_2C_6H_5$ | O | $COOC_6H_5$ |
| 6-$C_4H_9$ | N | O | $NCH_3$ | $COOC_2H_5$ |
| 6-$CH_2OH$ | N | S | $CHC_6H_5$ | $C_6H_5$ |
| 5-$NH_2$ | N | O | $CHCH_2C_6H_5$ | $C_3H_7CO$ |
| 5-$NHCH_3$ | N | O | O | H |
| 6-SH | N | O | O | $CH_3$ |
| 6-$SC_3H_7$ | N | S | N | $C_{10}H_7$ |
| 6-$C_4H_7$ | N | O | O | COOH |
| 6-$NO_2$ | N | O | O | H |
| 6-$C_6H_5CH_2O$ | N | O | O | H |
| 6-$OCF_3$ | N | O | O | H |
| 6-$C_2H_4NH_2$ | N | O | O | H |
| H | CH | O | O | H |
| H | $CH_2$ | CH | O | H |
| H | CH | S | O | H |

The present new heterocyclic compounds are therapeutically useful as such or can be employed in the form of salts in view of their basic nature. Thus, these esters form salts with a wide variety of acids, inorganic and organic, including therapeutically-acceptable acids. The salts with therapeutically-acceptable acids are, of course, useful in the preparation of formulations where water solubility is desired. The salts with therapeutically-unacceptable acids are particularly useful in the isolation and purification of the present new esters. Therefore, all acid salts of the present new esters are contemplated by the present invention.

The pharmaceutically-acceptable acid addition salts are of particular value in therapy. These include salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, succinic, arylsulfonic, e.g., p-toluenesulfonic acids, and the like. The pharmaceutically-unacceptable acid addition salts, while not useful for therapy, are valuable for isolation and purification of the new substances. Further, they are useful for the preparation of pharmaceutically-acceptable salts. Of this group, the more common salts include those formed with hydrofluoric and perchloric acids. Hydrofluoride salts are particularly useful for the preparation of the pharmaceutically-acceptable salts, e.g., the hydrochlorides, by solution in hydrochloric acid and crystallization of the hydrochloride salt formed. The perchloric acid salts are useful for purification and crystallization of the new products.

As therapeutic agents, the present new heterocyclic compounds are particularly useful as anti-allergy agents, acting via inhibition of mediator release. They are active orally in the passive cutaneous anaphylaxis (PCA) screen; and inhibit histamine release from passively sensitized rat mast cells.

The therapeutic agents of this invention may be administered alone or in combination with pharmaceutically-acceptable carriers, the proportion of which is determined by the solubility and chemical nature of the compound, chosen route of administration and standard pharmaceutical practice. For example, they may be administered orally in the form of tablets or capsules containing such excipients as starch, milk sugar, certain types of clay and so forth. They may be administered orally in the form of solutions which may contain coloring and flavoring agents or they may be injected parenterally, that is, intramuscularly, intravenously or subcutaneously. For parenteral administration, they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as other anti-allergy agents and the dosage level is of the same order of magnitude as is generally employed with these other therapeutic agents. The therapeutic dosage will generally be from 10 to 750 milligrams per day and higher although it may be administered in several different dosage units. Tablets containing from 10 to 250 mg. of active agent are particularly useful.

The following examples further illustrate the invention.

EXAMPLE 1

Ethyl-3-(2-benzoxazoyl)hydrazine carboxylate

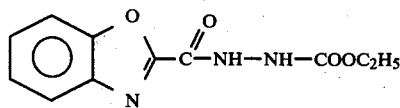

Method A

A mixture of 15 g. of 3-chloro-1,4-benzoxazin-2-one and 8.4 g. of ethyl carbazate in 80 ml. of dioxane and 12 ml. of triethylamine was stirred for 4 hours at room temperature. The organic solvent was evaporated and water (100 ml.) was added to the residue with stirring. The resulting solid was filtered and dried. Recrystallization from acetonitrile gave white crystals, m.p. 175°–176°.

Method B

A mixture of methylbenzoxazole-2-carboxylate (106 mg.) and ethyl carbazate (68.5 mg.) in dioxane was refluxed overnight. The organic solvent was evaporated and the residue extracted with hot hexane and ether to remove unreacted ester. Recrystallization from acetonitrile gave pure material, m.p. 175°–176°.

2-(2-oxo-3H-1,3,4-oxadiazole-5-yl)benzoxazole

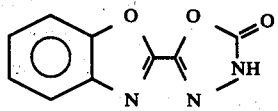

Twelve grams of the product prepared in accordance with Method A were added with stirring to Dowtherm A (250 ml.) at 230°–240°. After heating for one hour, the reaction mixture was cooled, filtered and the solid product washed with hexane. Recrystallization from acetonitrile gave analytical sample, m.p. 220°–223°.

In like manner as above, using appropriate starting materials and reagents, the following compounds were prepared:

5-chloro-2-(2-oxo-3H-1,3,4-oxadiazole-5-yl)benzoxazole, mp. 263°–266°.
5-carbomethoxy-7-methoxy-2-(2-oxo-3H-1,3,4-oxadiazole-5-yl)-benzoxazole, mp. 247°–248°.
6-methyl-2-(2-oxo-3H-1,3,4-oxadiazole-5-yl)benzoxazole, mp. 245°–248°.
5-carbethoxy-2-(2-oxo-3H-1,3,4-oxadiazole-5-yl)benzoxazole, mp. 218°–219°.
4-methyl-2-(2-oxo-3H-1,3,4-oxadiazole-5-yl)benzoxazole, mp. 247°–251°.
5-methyl-2-(2-oxo-3H-1,3,4-oxadiazole-5-yl)benzoxazole, mp. 207°–210°.
2-(2-oxo-3H-1,3,4-oxadiazole-5-yl)benzthiazole, mp. 235°–236°.

EXAMPLE 2

2-(2-oxo-3-acetyl-3H-1,3,4-oxadiazole-5-yl)benzoxazole

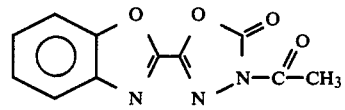

5.0 g of 2-(2-oxo-3H-1,3,4-oxadiazole-5-yl)benzoxazole in 50 ml of acetic acid containing 5 ml of acetic anhydride was heated for 1 hour at 100°. The mixture was poured into water and the crystalline product filtered. Recrystallization from acetonitrile gave mp. of 231°–232°.

In like manner as above, using appropriate starting materials and reagents, the following compounds were prepared:

2-(2-oxo-3-carbethoxy-3H-1,3,4-oxadiazole-5-yl)benzoxazole, mp. 189°–190°.
2-(2-oxo-3-carbethoxy-3H-1,3,4-oxadiazole-5-yl)-6-methyl benzoxazole, mp. 164°–166°.
2-(2-oxo-3-carbethoxy-3H-1,3,4-oxadiazole-5-yl)-1-methyl benzimidazole, mp. 179°–181°.
2-(2-oxo-3-acetyl-3H-1,3,4-oxadiazole-5-yl)-1-methyl benzimidazole, mp. 220°–222°.

EXAMPLE 3

Ethyl-3-(1-methyl-2-benzimidazoyl)-hydrazine carboxylate

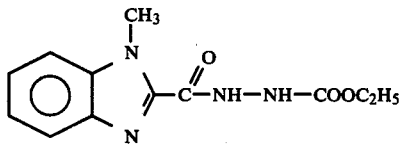

A mixture of 1-methyl-2-trichloromethyl benzimidazole (24.9 g., 0.1 mol), ethyl carbazate (10.4 g., 0.1 mol), acetonitrile (100 ml.), water (100 ml.) and sodium bicarbonate (33.6 g., 0.8 mol) was refluxed for 1 hour. After cooling the reaction was diluted with methylene chloride (200 ml.). The organic phase was separated, washed with water, dried (MgSO4) and concentrated to a solid, m.p. 190°–193° C.

1-Methyl-2-(1,3,4-oxadiazol-2(3H)-one-5-yl)benzimidazole

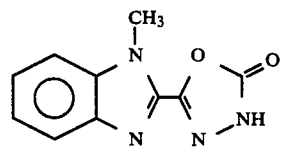

A suspension of 10 g. (0.046 m.) of the product from EXAMPLE 3 in "Dowtherm" (30 ml.) was heated at 180° C. for 30 minutes. The reaction was filtered hot. After cooling, the precipitate was washed with ether and recrystallized from acetone, m.p. 300° C.

EXAMPLE 4

Methyl-2(1-methyl)benzimidazolecarboxylate

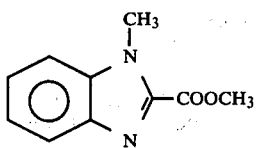

A solution of 1-methyl-2-trichloromethyl benzimidazole (249.5 g., 1 mol) in methanol (1.0 l) was refluxed for 2 days. The mixture was concentrated in vacuo and water (200 ml.) was added. The resulting suspension was neutralized with sodium bicarbonate (250 g.) and extracted with chloroform (3×200 ml.). The organic phase was separated, dried (MgSO₄) and concentrated to a solid, m.p. 99.0°–99.5° C.

2-(1-methyl-2-benzimidazoyl)hydrazine

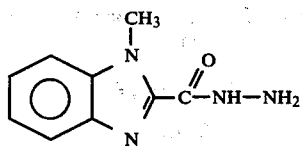

To a solution of methyl-2-(1-methyl)benzimidazole carboxylate (95 g., 0.5 mol) in isopropanol (500 ml.) was added an aqueous solution (85%) of hydrazine (190 ml.). The reaction was heated at 60° C. for 1 hour and then cooled to 0° C. The resulting precipitate was filtered, washed (ether) and dried, m.p. 156°–159° C.

1-Methyl-2(1,3,4-oxadiazole-2(3H)-one-5-yl)benzimidazole

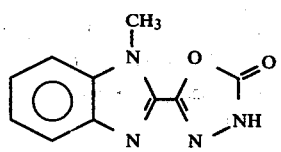

Phosphene gas was slowly dispersed through a suspension of 2-(1-methyl-2-benzimidazole)hydrazine (95 g., 0.5 mol) in methylene chloride (300 ml.) until saturated. After stirring for 1 hour, the precipitate was filtered, washed (CH₂Cl₂) and dried. The solid thus obtained is the hydrochloride salt (mp. 253–261 decomposes) which can be converted to the free base (mp. 300° C.) by treatment with aqueous sodium bicarbonate.

In the same way as above, 3-chlorobenzo(b)thiophene 2-carboxylic acid hydrazide was reacted with phosgene to give 3-chloro-2-(2-oxo-3H-1,3,4-oxadiazole-5-yl)-benzo(b)thiophene, mp. 218°–220°.

In the same way as above, ethyl-indene-2-carboxylate was reacted with hydrazine and phosgene to give 2-(2-oxo-3H-1,3,4-oxadiazole-5-yl)indene.

EXAMPLE 5

1-Methyl-2(1,3,4-triazole-2(1H,3H)-one-5-yl)benzimidazole

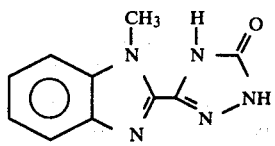

A mixture of 1-methyl-2-trichloro-methyl benzimidazole (23.7 g., 0.1 mol), semicarbazide (7.5 g., 0.1 mol), triethylamine (50 ml.), water (100 ml.) and acetonitrile (200 ml.) was refluxed for 5 hours. The reaction was filtered hot giving 4.1 g. of crude product. This material was purified by treating with methanol at reflux for ½ hour and filtering hot giving a white solid, mp. 293°–296°.

EXAMPLE 6

2-(2-oxo-3H-1,3,4-oxadiazole-5-yl)benzofuran

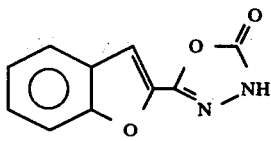

To a solution of 2-chlorocarbonyl benzofuran (45 g., 0.25 mol) in acetonitrile (500 mls.) was added ethyl carbazate (27 g., 0.26 mol). After heating at reflux for 1 hour, the reaction was cooled to 0° C. for 18 hours. The precipitate was filtered, washed (ether) and dried to give ethyl-3-(2-benzofuranoyl)hydrazine carboxylate, mp. 137°–138°. 4.0 g. (16 mmoles) of this product in Dowtherm A was heated at 240° C. for 4 hours. After cooling, the reaction was filtered. The product was purified by HPLC using 3:1 hexane/acetone to give a white powder, mp. 202°–203° C.

EXAMPLE 7

2-(1,3,4-triazole-2-(1H,3H)-one-5-yl)-benzoxazole

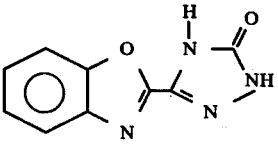

Methyl benzoxazole-2-imidate, 8.0 g. and 5.2 g. of ethyl carbazate in 60 ml. of dioxane was heated at 110° overnight. After evaporation of solvent, the residue was suspended in 45 ml. of Dowtherm A and heated at 220° for 15 minutes. The precipitated product was filtered, washed with CH₂Cl₂, CH₃OH, and dried to give 3.6 g. of solid, mp. >300°.

EXAMPLE 8

2-(2-oxo-3H-1,3,4-thiadiazole-5-yl)indene

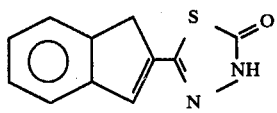

Ethyl indene-2-carboxylic acid hydrazide, (17.4 g., 0.1 mol) in 200 ml. of carbon disulfide was treated with 22 g. (0.1 mol) of phosphorous pentasulfide, and the mixture stirred at reflux for 24 hours. The mixture was extracted with 3 portions of 10% sodium hydroxide solution and the organic phase was dried and concentrated to a solid. The thiohydrazide thus prepared was reacted with phosgene as described in EXAMPLE 4 to give the title product.

EXAMPLE 9

2-(pyrazole-5-(1H,4H)one-3-yl)benzoxazole

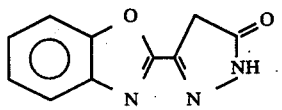

Fifty percent sodium hydride in mineral oil (5.28 g., 0.11 mole) was washed twice with heptane and suspended in 100 ml. of dry THF. Ethyl acetate, 9.68 g. (0.11 mole) was added, and the mixture stirred at reflux for 4 hours. There was then added dropwise 18.2 g. (0.1 mole) of 2-chlorocarbonylbenzofuran. The mixture was stirred at room temperature for 16 hours, diluted with water and the THF removed by distillation. The aqueous phase was extracted with chloroform, and the chloroform phase concentrated to a gum. This was taken up in 100 ml. of ethanol, treated with 5.0 g. of 85% hydrazine hydrate, and the solution refluxed for 4 hours. The mixture was concentrated to a gum which crystallized on rubbing and was recrystallized from ethanol to give the title product.

The compounds of this invention have potent activity in inhibiting the formation of a wheal when screened according to the Rat Passive Cutaneous Anaphylaxis (PCA) Screen as described by I. Mota, Life Sciences, 7, 465 (1963) and Z. Ovary, et al., Proceedings of Society of Experimental Biology and Medicine, 81, 584 (1952).

In addition, the compounds of this invention have potent activity as inhibitors of histamine release from passively sensitized Rat Mast Cells according to the procedure described by E. Kusner, et al., Journal of Pharmacology and Experimental Therapeutics.

What is claimed is:

1. An anti-allergic compound of the formula

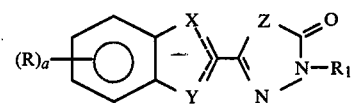

wherein:
the dotted line indicates that the double bond may be in either position;
R is hydrogen, alkyl, alkenyl, alkoxy, alkenyloxy, aryloxy, aralkoxy, halogen, cyano, nitro, carboxy, hydroxy, formyl, carbalkoxy, hydroxyalkyl, amino, alkylamino, trifluoromethyl, mercapto, trifluoromethoxy, alkylthio, or aminoalkyl, wherein the number of carbon atoms in the alkyl and alkenyl moieties is up to 7 and in the aryl moieties is up to 10;
Y is N, N—$R_2$ or $CR_2$ wherein $R_2$ is hydrogen, alkyl or aryl and the number of carbon atoms is up to 7 in said alkyl moiety and is up to 10 in the aryl moiety, with the proviso that when Y is NH, $(R)_a$ is not hydrogen;
a is an integer from 1 to 4;
X and Z are independently O, S, $NR_2$ or $CR_2$ wherein $R_2$ is as defined above, with the proviso that when Y is $NR_2$, X is not $CR_2$; and
$R_1$ is hydrogen, alkyl, aryl, acyl, carbalkoxy, or carbaryloxy, wherein the number of carbon atoms in is up to 7 in the alkyl and aliphatic acyl groups and is up to 10 in the aryl and aromatic acyl groups; and acid addition salts thereof.
2. A compound according to claim 1 wherein Z is O.
3. A compound according to claim 2 wherein Y is N and $R_2$ is alkyl or aryl.
4. A pharmaceutical composition comprising a compound as claimed in claim 1 in a pharmaceutically-acceptable excipient.
5. The compound according to claim 3 wherein R is alkyl; a is 1; X is O and $R_1$ is H.
6. The compound according to claim 3 wherein R is H; X is O and $R_1$ is alkyl.
7. The compound according to claim 3 wherein R is Cl; a is 1; X is O and $R_1$ is H.
8. The compound according to claim 3 wherein R is H; X is N-alkyl; and $R_1$ is acyl.
9. The compound according to claim 3 wherein R is H; X is N-alkyl; and $R_1$ is H.
10. The compound according to claim 3 wherein R is H; X is S and $R_1$ is H.
11. A compound according to claim 3 wherein X is CH, Y is O and R is alkyl.
12. 2-(2-Oxo-3H-1,3,4-oxadiazol-5-yl)benzoxazole.
13. 1-Methyl-2-(2-oxo-3H-1,3,4-oxadiazol-5-yl)-benzimidazole.
14. 5-Chloro-2-(2-oxo-3H-1,3,4-oxadiazol-5-yl)-benzoxazole.
15. 6-Methyl-2-(2-oxo-3H-1,3,4-oxadiazol-5-yl)-benzoxazole.
16. 2-(2-Oxo-3H-1,3,4-oxadiazol-5-yl)benzothiazole.
17. 2-(2-Oxo-3-acetyl-3H-1,3,4-oxadiazol-5-yl)-1-methylbenzimidazole.
18. 2-(2-Oxo-3H-1,3,4-oxadiazole-5-yl)benzofuran.
19. An acid addition salt of the compound of claim 9.
20. An acid addition salt of the compound of claim 11.
21. An acid addition salt of the compound of claim 16.

* * * * *